United States Patent
Heveling et al.

[11] Patent Number: 6,040,457
[45] Date of Patent: Mar. 21, 2000

US006040457A

[54] PROCESS FOR THE PREPARATION OF FORMYLIMIDAZOLES

[75] Inventors: Josef Heveling, Naters; Alain Wellig, Kanton Wallis, both of Switzerland

[73] Assignee: Lonza AG, Gampel/Valais, Switzerland

[21] Appl. No.: 09/192,372

[22] Filed: Nov. 16, 1998

[30] Foreign Application Priority Data

Nov. 14, 1997 [CH] Switzerland ............... 2637/97

[51] Int. Cl.[7] ............................................. C07D 233/64
[52] U.S. Cl. ............................................. 548/333.5
[58] Field of Search ........................................ 548/332.1

[56] References Cited

U.S. PATENT DOCUMENTS

| | | | |
|---|---|---|---|
| 4,026,907 | 5/1977 | Scott et al. | 260/345.5 |
| 5,336,779 | 8/1994 | Yamamoto et al. | 548/333.5 |
| 5,552,427 | 9/1996 | Matsutani et al. | 514/398 |

FOREIGN PATENT DOCUMENTS

| | | |
|---|---|---|
| 0139421 | 5/1985 | European Pat. Off. . |
| 0146228 | 6/1985 | European Pat. Off. . |
| 0645383 | 3/1995 | European Pat. Off. . |
| 0891974 | 1/1999 | European Pat. Off. . |
| 2681323 | 3/1993 | France ............... 548/332.1 |
| 6-239837 | 8/1994 | Japan . |
| 6-256313 | 9/1994 | Japan . |
| 685496 | 9/1993 | Switzerland . |
| WO 92/20651 | 11/1992 | WIPO . |

OTHER PUBLICATIONS

E.F. Godefroi et al., Trav. Chim. Receuil Pays–Bas, 91, 1383, (1972).

McKillop, "Comprehensive Heterocyclic Chemistry II", vol. 5, (1996), pp. 403 to 406.

*Primary Examiner*—Floyd D. Higel
*Attorney, Agent, or Firm*—Fisher, Christen & Sabol

[57] ABSTRACT

A process for the catalytic conversion of hydroxymethylimidazoles to formylimidazoles. The catalysis takes place in the presence of a peroxide. Formylimidazoles are important intermediates for pharmaceutical active ingredients.

14 Claims, No Drawings

PROCESS FOR THE PREPARATION OF FORMYLIMIDAZOLES

BACKGROUND OF THE INVENTION

1 Field Of The Invention

The invention relates to a novel process for the preparation of formylimidazoles of the general formula:

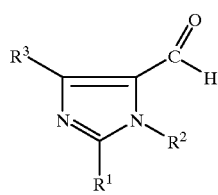

or

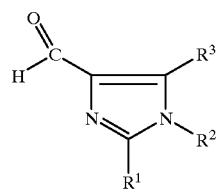

in which $R^1$ is hydrogen or an optionally substituted alkyl group, $R^2$ is hydrogen, or an optionally substituted alkyl, aryl or arylalkyl group, and $R^3$ is hydrogen or an optionally substituted alkyl group, by catalytic oxidation of hydroxymethylimidazoles of the general formula:

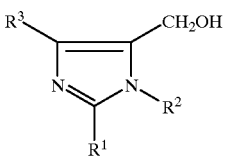

or

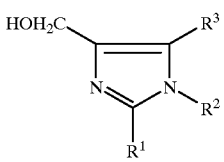

in which $R^1$, $R^2$ and $R^3$ are as defined above.

2. Background Art

Formylimidazoles are important intermediates, for example, for the preparation of pharmaceutical active ingredients, such as, diuretics or antihypertensives (International Published Patent Application No. WO-A 92/20651). Several processes for the preparation of formylimidazoles are know to date. Swiss Patent No. 685, 496 describes a process in which the catalytic oxidation of hydroxymethylimidazoles to formylimidazoles is carried out in the presence of noble-metal catalysts, such as, platinum-bismuth, platinum black, platinum or palladium on activated carbon, while passing in oxygen. Disadvantages of this process are the long reaction times of several hours and the formation of by-products.

BROAD DESCRIPTION OF THE INVENTION

The object of the invention is to provide an economical process for the preparation of formylimidazoles which does not have the above-described disadvantages.

This object is achieved by the process according to the invention.

Hydroxymethylimidazoles of the general formula:

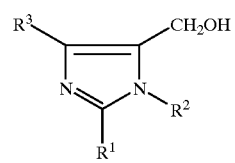

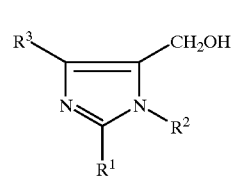

or

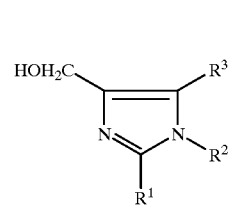

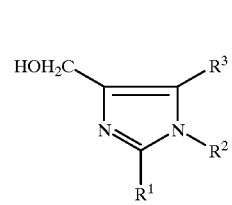

in which $R^1$, $R^2$ and $R^3$ are as defined above, are catalytically oxidized in the presence of a noble-metal catalyst and a peroxide to formlimidazoles of the general formula:

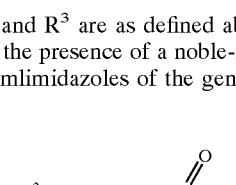

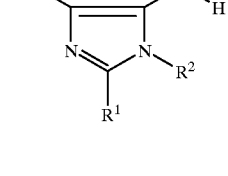

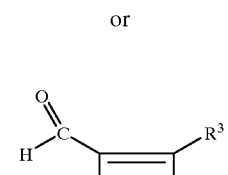

or

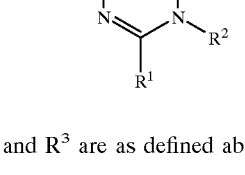

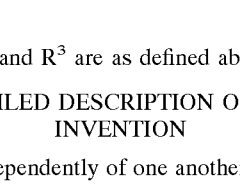

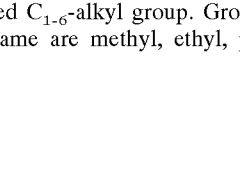

in which $R^1$, $R^2$ and $R^3$ are as defined above.

DETAILED DESCRIPTION OF THE INVENTION $R^1$ and $R^2$ independently of one another are hydrogen or an optionally substituted alkyl group, in particular a straight-chain or branched $C_{1-6}$-alkyl group. Groups which can be mentioned by name are methyl, ethyl, propyl, isopropyl, butyl, isobutyl, tert-butyl, pentyl and its isomers and hexyl and its isomers. $R^2$ can also be optionally substituted aryl or arylalkyl, in particular phenyl or phenylalkyl, in which case phenylalkyl is preferably taken to mean phenyl $C_{1-6}$-alkyl, particularly preferably benzyl. Expedient substituents of the alkyl groups or of the aromatic system of the aryl function are, for example, halogen, amino, alkylamino, dialkylamino, alkoxy or hydroxyl, alkyl preferably being, as above, $C_{1-6}$-alkoxy, for example methoxy or ethoxy. Halogen as used herein is taken to mean fluorine, chlorine, bromine or iodine. In particularly preferred meanings, $R^1$ is butyl and $R^2$ is hydrogen.

$R^3$ is hydrogen or an optionally substituted alkyl group, in particular a straight-chain or branched $C_{1-6}$-alkyl group. Groups which can be mentioned by name are methyl, ethyl, propyl, isopropyl, butyl, isobutyl, butyl, tert-butyl, pentyl and its isomers and hexyl and its isomers. The substitutes can be those given above. $R^3$ is particularly preferably hydrogen.

The starting hydroxymethylimidazoles can be prepared in a simple manner, for example, according to the procedure in WO-A 92/20651 or according to E. F. Godefroi et al., Trav. Chim. Receuil Pay-Bas, 91, 1383 (1972).

The noble-metal catalyst can be platinum, palladium, rhodium or gold. The noble metal is expediently used in combination with metals, such as, bismuth, lead, cerium or indium, as a second component. Preference is given to platinum/bismuth or platinum/lead catalysts. The noble metal catalyst is used as such or bonded to a support material, such as, activated carbon, silicon dioxide, aluminium oxide, silicon aluminium oxide, zirconium oxide or titanium oxide. It is preferably bonded to activated carbon. Noble-metal catalysts which are bonded to activated carbon are available commercially, for example, from Degussa. The amount of noble metal bonded to a support material is expediently between 0.1 and 15 percent by weight, preferably between 0.5 and 7 percent by weight, based on the support material. The noble-metal catalyst is preferably used in an amount of from 0.05 to 1.0 mol percent based on the noble metal, relative to the hydroxymethylimidazole, and particularly preferably in an amount of from 0.1 to 0.4 mol percent based on the noble metal, relative to the hydroxymethylimidazole.

The peroxides used are organic or inorganic peroxides. Examples of suitable peroxides are hydrogen peroxide, perborates, a percarboxylic acid, tert-butyl hydroperoxide, cumene hydroperoxide, perbenzoic acid, m-chloroperbenzoic acid, monoperphthalic acid or peracetic acid. A particularly suitable peroxide is hydrogen peroxide, which is expediently used as a 10 to 30 percent strength aqueous solution.

The catalytic oxidation expediently takes place in the presence of water, a water-miscible solvent, a water-immiscible organic solvent or mixtures thereof, in an alkaline medium. Examples of suitable water-miscible solvents are alcohols or carboxylic acids having from 1 to 6 carbon atoms, or ketones, such as, acetone or methyl ethyl ketone. Examples of suitable water-immiscible organic solvents are isobutyl methyl ketone or ethyl acetate. Preference is given to water.

It has been found advantageous to produce the alkaline medium by adding an alkali metal hydroxide, an alkali metal carbonate or an alkali metal acetate to the reaction mixture. Alkali metal hydroxide is preferably used in the ratio from 1:0.05 to 1:1.2, preferably from 1:0.1 to 1:1, based on the molar amount used of the hydroxymethylimidazole of the general formula III or IV.

The catalytic oxidation expediently takes place at a temperature of 20° to 120° C., advantageously at 50° to 80° C.

After a customary peroxide metering time of approximately 1 hour it is possible, after a sufficient post-reaction time, to isolate the compound of the general formula I or II in a manner customary to the person skilled in the art.

The product is expediently isolated, depending on the solvent system, either by crystallization and filtration or by extraction with a suitable solvent. The catalyst used can be used repeatedly without loss of activity.

EXAMPLE 1

Preparation of 2-n-butyl-5-formylimidazole 1.5 g of 2-n-butyl-5-hydroxymethylimidazole, 1.5 g of dodecane as internal GC standard, 0.3 g of 5 percent platinum and 5 percent bismuth on activated carbon (comprising 61.3 percent water), 20 g of isobutyl methyl ketone and 2.5 g of 1.6 percent strength NaOH solution were heated to about 58° C. with stirring. At 58° to 64° C., 2.9 g of 15.7 percent strength aqueous $H_2O_2$ solution was added dropwise over the course of 45 min. The reaction mixture was then allowed to react for 15 min and then filtered. The filtrate was transferred to a separating funnel, the $H_2O$ phase was separated off, the organic phase was concentrated and cooled, and the product crystallized out and was filtered off. The yield was determined by GC (internal standard). The reaction yield was 88.2 percent (6.75 percent of starting material).

EXAMPLE 2

Preparation of 2-n-butyl-5-formylimidazole 2.0 g of 2-n-butyl-5-hydroxymethylimidazole, 0.3 g of 5 percent platinum and 5 percent bismuth on activated carbon (comprising 61.3 percent water), 13 ml of 1 N NaOH solution and 7 g of $H_2O$ were heated to about 60° C. with stirring. At 60° to 64° C., 3.4 g of 15 percent strength aqueous $H_2O_2$ solution was added dropwise over the course of 45 min. The reaction mixture was then allowed to react for 15 min and then filtered. The pH of the filtrate was adjusted from 13.4 to 9.0 using 20 percent $H_2SO_4$, as a result of which a pale yellow suspension formed. This was cooled, and the crude product was able to be filtered off and/or extracted with methylene chloride. The reaction was monitored by GC analysis. The reaction yield was 100 percent (0 percent of starting material).

EXAMPLE 3

Preparation of 2-n-butyl-5-formylimidazole

The procedure described in Example 2 was repeated but using 0.3 g of 5 percent platinum and 5 percent lead on activated carbon (comprising 55.7 percent of water) instead of 0.3 g of 5 percent platinum and 5 percent bismuth on activated carbon. The reaction yield was 99.5 percent (0.5 percent of by-products).

EXAMPLE 4

Preparation of 2-n-butyl-5-formylimidazole 4.0 g of 2-n-butyl-5-hydroxymethylimidazole, 0.6 g of 5 percent platinum and 5 percent bismuth on activated carbon (comprising 61.3 percent water), and 25.6 ml of 1N NaOH solution were heated to about 60° C. with stirring. At 60° to 64° C., 6.8 g of 15 percent strength aqueous $H_2O_2$ solution was added dropwise over the course of 45 min. The reaction mixture was then allowed to react for 15 min and then filtered off. The pH of the filtrate was adjusted from 13.2 to 9.0 using 20 percent $H_2SO_4$, as a result of which a yellow suspension formed. This was cooled, and the crude product was able to be filtered off and/or extracted with methylene chloride. The reaction was monitored by GC analysis. The reaction yield was 98.2 percent (1.8 percent of starting material).

EXAMPLE 5

Preparation of 2-n-butyl-5-formylimidazole

The procedure described in Example 4 was repeated but 15 percent strength aqueous $H_2O_2$ solution was added dropwise at 50° to 54° C., instead of at 60° to 64° C. The reaction yield was 97.6 percent (2.4 percent of starting material).

EXAMPLE 6

Preparation of 2-n-butyl-5-formylimidazole

The procedure described in Example 4 was repeated but 15 percent strength aqueous $H_2O_2$ solution was added dropwise at 70° to 74° C., instead of at 60° to 64°C. The reaction yield was 97.7 percent (2.1 percent of starting material).

EXAMPLE 7

Preparation of 2-n-butyl-5-formylimidazole Starting From The Crude Starting Material 4.4 g of 2-n-butyl-5-hydroxymethylimidazole (crude starting material, 90.4 percent), 0.6 g of 5 percent platinum and 5 percent bismuth on activated carbon (comprising 61.3 percent water), 25.6 ml of 1N NaOH solution and 5 ml of methanol were heated to about 60° C. with stirring. At 60° to 64° C., 6.8 g of 15 percent strength aqueous $H_2O_2$ solution was added dropwise over the course of 45 min. The reaction mixture was then allowed to react for 15 min and then filtered. The pH of the filtrate was adjusted from 13.0 to 9.0 using 20 percent $H_2SO_4$, as a result of which a yellow suspension formed. This was cooled, and the crude product was able to be filtered off and/or extracted with methylene chloride. The reaction was monitored by GC analysis. The reaction yield was 94.5 percent (3.5 percent of starting material).

EXAMPLE 8

(Comparative Experiment According to Swiss Patent No. 685,946, Using Air as the Oxidizing Agent)

Preparation of 2-n-butyl-5-formylimidazole 4.6 g of 2-n-butyl-5-hydroxymethylimidazole, 4.6 g of dodecane as internal GC standard, 0.6 g of 5 percent platinum and 5 percent bismuth on activated carbon (comprising 61.3 percent water), 42 g of isobutyl methyl ketone and 7.5 g of 1.6 percent strength NaOH solution were heated to about 80° C. with stirring. At 80° C., 3.6 liters (STP) of air/hour was introduced into the solution until the absorption of oxygen was complete (350 min!). The reaction mixture was filtered. The filtrate was transferred to a separating funnel, the $H_2O$ phase was separated off, the organic phase was concentrated and cooled, and the product crystallized out and was filtered off. The reaction was monitored using GC analysis (internal standard). The reaction yield was 90.0 percent (0.3 percent of starting material).

EXAMPLE 9

(Catalyst Recycle)

20.9 g of 2-n-butyl-5-hydroxymethylimidzole (crude starting material, 95.3 percent), 3.2 g of 5 percent platinum and 5 percent lead on activated carbon (comprising 55.7 percent of water), 130 ml of 1N NaOH solution and 22 ml of methanol were heated to about 60° C. with stirring. At 60° C., 22.5 g of 20 percent strength aqueous $H_2O_2$ solution was added dropwise over the course of 60 min. The reaction mixture was then allowed to react for 10 min and then filtered. The pH of the filtrate was adjusted from 12.8 to 7.5 using 50 percent $H_2SO_4$, as a result of which a yellowish suspension formed. The methanol and some water were distilled off, the suspension was cooled to 2° C., and the product was filtered off. The product was dried at 65° C. and 30 mbar. After the catalyst was used for the first time, 18 g of a pale yellow substance was isolated (content: 98.5 percent, HPLC percent by weight). The isolated yield was 90 percent. The ability of the catalyst to be used again was monitored using GC analysis (standard percent). The catalyst was used a total of eight times. The catalyst losses were not replaced.

The results of Example 9 are given in the following table:

TABLE 1

| Catalyst Use | 2-n-butyl-5-formylimidazole [GC standard %] | Unreacted 2-n-butyl-5-hydroxymethylimidazole [GC standard %] |
|---|---|---|
| 1 | 97.9 | 1 |
| 2 | 97.5 | 1.3 |
| 3 | 97.0 | 1.9 |
| 4 | 97.5 | 1.7 |
| 5 | 98.0 | 0 |
| 6 | 97.2 | 1.7 |
| 7 | 95.9 | 2.9 |
| 8 | 96.6 | 1.9 |

What is claimed is:

1. A process for the preparation of a formylimidazole of the formula:

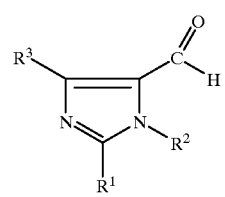

I or

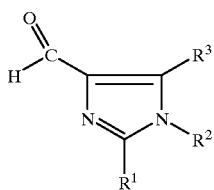

II in which $R^1$ is hydrogen or an unsubstituted or substituted alkyl group, $R^2$ is hydrogen, or an unsubstituted or substituted alkyl, aryl or arylalkyl group, and $R^3$ is hydrogen or an unsubstituted or substituted alkyl group, comprising catalytically oxidizing a hydroxymethylimidazole of the formula:

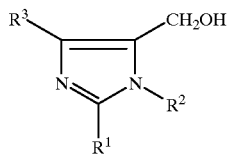

III or

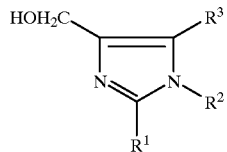

IV in which $R^1$, $R^2$ and $R^3$ are as defined above, in the presence of a noble-metal catalyst, the catalytic oxidation taking place in the presence of a peroxide.

2. The process according to claim 1, wherein $R^1$ is a butyl group.

3. The process according to claim 2, wherein $R^2$ and $R^3$ are hydrogen.

4. The process according to claim 3, wherein the noble-metal catalyst is a platinum/bismuth catalyst or a platinum/lead catalyst.

5. The process according to claim 4, wherein the peroxide is hydrogen peroxide.

6. The process according to claim 5, wherein the catalytic oxidation is carried out in the presence of water, a water-miscible solvent, a water-immiscible organic solvent or mixtures thereof, in an alkaline medium.

7. The process according to claim 6, wherein the alkaline medium is obtained by adding an alkali metal hydroxide, an alkali metal carbonate or an alkali metal acetate to the reaction mixture.

8. The process according to claim 7, wherein the reaction is carried out at a temperature of 20° to 1 20° C.

9. The process according to claim 1, wherein $R^2$ and $R^3$ are hydrogen.

10. The process according to claim 1, wherein the noble-metal catalyst is a platinum/bismuth catalyst or a platinum/lead catalyst.

11. The process according to claim 1, wherein the peroxide is hydrogen peroxide.

12. The process according to claim 1, wherein the catalytic oxidation is carried out in the presence of water, a water-miscible solvent, a water-immiscible organic solvent or mixtures thereof, in an alkaline medium.

13. The process according to claim 12, wherein the alkaline medium is obtained by adding an alkali metal hydroxide, an alkali metal carbonate or an alkali metal acetate to the reaction mixture.

14. The process according to claim 1, wherein the reaction is carried out at a temperature of 20° to 120° C.

* * * * *